(12) United States Patent
Hüsler et al.

(10) Patent No.: US 7,723,397 B2
(45) Date of Patent: May 25, 2010

(54) DIFUNCTIONAL PHOTOINITIATORS

(75) Inventors: Rinaldo Hüsler, Basel (CH); André Fuchs, Schliengen-Obereggenen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 960 days.

(21) Appl. No.: 10/521,650

(22) PCT Filed: Jul. 10, 2003

(86) PCT No.: PCT/EP03/07482

§ 371 (c)(1), (2), (4) Date: Jan. 13, 2005

(87) PCT Pub. No.: WO2004/009651

PCT Pub. Date: Jan. 29, 2004

(65) Prior Publication Data

US 2005/0239971 A1    Oct. 27, 2005

(30) Foreign Application Priority Data

Jul. 19, 2002  (EP)  ................... 02405632

(51) Int. Cl.
*C08F 2/50* (2006.01)
*C08F 2/46* (2006.01)
*C08J 3/28* (2006.01)

(52) U.S. Cl. ............... 522/36; 522/70; 522/33; 522/113; 522/116; 522/120; 522/173; 522/178; 522/182; 522/909; 568/397; 568/410; 568/336; 427/508; 427/510; 427/511; 427/517; 427/520

(58) Field of Classification Search .......... 522/36, 522/60; 568/397, 410, 336; 427/508, 510, 427/511, 517, 520
See application file for complete search history.

(56) References Cited

U.S. PATENT DOCUMENTS

| | | | | |
|---|---|---|---|---|
| 3,844,916 A | * | 10/1974 | Gaske | 522/33 |
| 4,048,034 A | * | 9/1977 | Martan | 522/39 |
| 4,308,400 A | | 12/1981 | Felder et al. | 568/336 |
| 4,315,807 A | | 2/1982 | Felder et al. | 204/159.18 |
| 4,318,791 A | | 3/1982 | Felder et al. | 204/159.23 |
| 4,321,118 A | | 3/1982 | Felder et al. | 204/159.18 |
| 2005/0004249 A1 | | 1/2005 | Fuchs et al. | 522/36 |

FOREIGN PATENT DOCUMENTS

EP    0262242    6/1988

OTHER PUBLICATIONS

C. Groenenboom et al., Journal of Photochemistry and Photobiology A: Chemistry, vol. 107, (1997), pp. 261-269.

* cited by examiner

*Primary Examiner*—Sanza L McClendon
(74) *Attorney, Agent, or Firm*—Shiela A. Loggins

(57) ABSTRACT

The invention relates to novel photoinitiators of formula (I) wherein A is —O—, —$CH_2$—, $CH(CH_3)$— or —$C(CH_3)_2$—, and R is methyl or trimethylsilyl, and R may in addition be hydrogen when A is simultaneously the group —$C(CH_3)_2$—. The invention relates also to compositions comprising (A) at least one ethylenically unsaturated compound, (B) a photoinitiator of formula (I), (C) optionally further binders or additives, (D) optionally further photoinitiators or co-initiators. Compositions comprising (A) an ethylenically unsaturated compound that contains at least one aminoacrylate, (B) a photoinitiator of formula (II) or (III), (C) optionally further binders or additives, (D) optionally further photoinitiators or co-initiators.

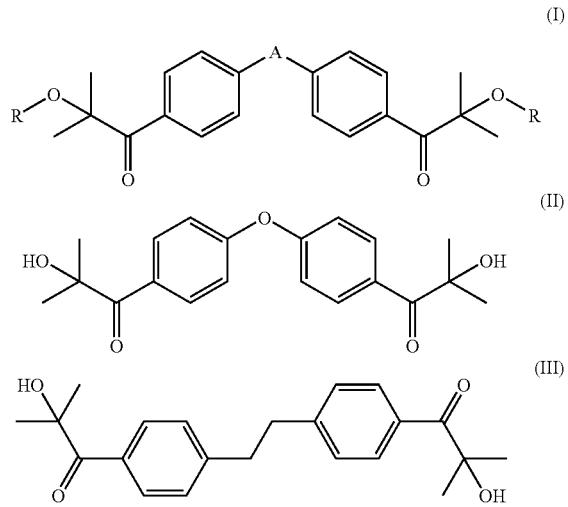

6 Claims, No Drawings

DIFUNCTIONAL PHOTOINITIATORS

The invention relates to new difunctional photoinitiators and to the use thereof. The invention relates also to aminoacrylate-containing systems that comprise novel and known photoinitiators.

UV curing systems can be used in a large number of applications, e.g. in printing inks, overprint coatings, in the production of printing plates and coatings of all kinds. The use of a photoinitiator from which reactive particles, such as free radicals or cations (protons), are generated by means of interaction with UV radiation is necessary for the efficient polymerisation of such systems. A disadvantage of the photoinitiators frequently used in practice today, such as DAROCUR 1173 and IRGACURE 184, is their strong odour, which is caused chiefly by the products formed in the course of the UV-induced cleavage of such photoinitiators. There is accordingly a need for low-odour photoinitiators, which need is met by only few commercially available products, such as ESACURE KIP 150 (Lamberti) and IRGACURE 2959 (Ciba Spezialitätenchemie).

Both of those products have disadvantages that make their use more complicated: ESACURE KIP 150 is a solid that is tacky at room temperature and therefore presents handling problems; IRGACURE 2959 has a comparatively low solubility in current formulations.

A further important criterion for the use of photoinitiators is how effectively they enable the formulation constituents in question to be polymerised. This has a direct effect on the rate of curing in the production process and on the degree of crosslinking of the polymerisable constituents of the formulation.

European Patent Application EP-A 003 002 describes the use of specific ketones as photoinitiators. The ketones have a tertiary alpha C atom that is substituted by a hydroxyl or amino group or an etherification or silylation product thereof. The compound 4,4'-bis(alpha-hydroxy-isobutyryl)diphenyl oxide is named as an example.

It has now been found that α-substituted ketones of the formula I below are surprisingly highly effective in aminoacrylate-containing compositions and, in addition, possess the above-required properties as photoinitiators.

The invention accordingly relates to novel photoinitiators of formula I

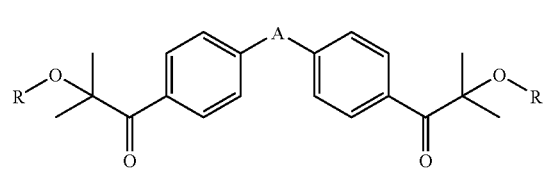

wherein
A is —O—, —CH$_2$—, —CH(CH$_3$)— or —C(CH$_3$)$_2$—, and
R is methyl or trimethylsilyl, and R may in addition be hydrogen when A is simultaneously the group —C(CH$_3$)$_2$—.

Preference is given to compounds of formula I wherein A is —O—, —CH$_2$— or —CH(CH$_3$)— and R is methyl.

The invention accordingly relates also to a composition comprising
(A) at least one ethylenically unsaturated compound,
(B) a photoinitiator of formula I,
(C) optionally further binders or additives,
(D) optionally further photoinitiators or co-initiators.

The compounds of formula I are suitable especially as photoinitiators in ethylenically unsaturated compounds that contain at least one aminoacrylate and in formulations for printing inks.

The invention accordingly relates also to a composition comprising
(A) an ethylenically unsaturated compound that contains at least one aminoacrylate,
(B) a photoinitiator of formula I,
(C) optionally further binders or additives,
(D) optionally further photoinitiators or co-initiators.

It is equally surprising that the photoiniators of formula I exhibit high reactivity in formulations for printing inks in which otherwise α-aminoketones or benzophenone/amine mixtures are state of the art. α-Hydroxyketones such as IRGACURE 184 or DAROCUR 1173 are not sufficiently reactive in such formulations.

It has furthermore been found that known compounds of formula II or III

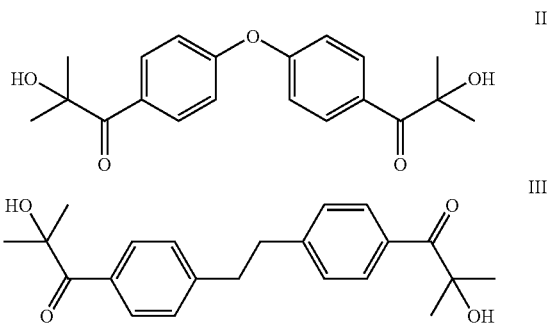

likewise exhibit an extraordinarily high level of effectiveness in formulations that contain amine-modified polyfunctional acrylates and in formulations for printing inks.

The invention accordingly relates also to a composition comprising
(A) an ethylenically unsaturated compound that contains at least one aminoacrylate,
(B) a photoinitiator of formula II or III
(C) optionally further binders or additives,
(D) optionally further photoinitiators or co-initiators.

Suitable Ethylenically Unsaturated Compounds (A)

The unsaturated compounds (A) may contain one or more olefinic double bonds. They may be low molecular weight (monomeric) or higher molecular weight (oligomeric).

Examples of monomers having one double bond include alkyl and hydroxyalkyl acrylates and methacrylates, for example methyl, ethyl, butyl, 2-ethylhexyl and 2-hydroxyethyl acrylate, isobornyl acrylate, methyl methacrylate and ethyl methacrylate. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having a plurality of double bonds include ethylene glycol diacrylate, propylene glycol diacrylate, neopentyl glycol diacrylate, hexamethylene glycol diacrylate and bisphenol-A diacrylate, 4,4'-bis(2-acryloyloxyethoxy)diphenylpropane, trimethylolpropane triacrylate, pentaerythritol triacrylate, pentaerythritol tetraacrylate, vinyl acrylate, divinyl-benzene, divinyl succinate, diallyl phthalate, triallyl phosphate, triallyl isocyanurate and tris(2-acryloylethyl) isocyanurate.

Examples of higher molecular weight (oligomeric) polyunsaturated compounds include acrylated epoxy resins, acrylated or vinyl ether or epoxy group-containing polyesters, polyurethanes and polyethers.

Further examples of unsaturated oligomers include unsaturated polyester resins, which are usually prepared from maleic acid, phthalic acid and one or more diols and have molecular weights of about from 500 to 3000. In addition, it is also possible to use vinyl ether monomers and oligomers, and also maleate-terminated oligomers having polyester, polyurethane, polyether, polyvinyl ether and epoxide main chains. Combinations of vinyl ether group-carrying oligomers and polymers, as described in WO 90/01512, are especially suitable, but copolymers of monomers functionalized with maleic acid and vinyl ether also come into consideration.

Also suitable are compounds having one or more free-radical-polymerizable double bonds. Preferably, the free-radical-polymerizable double bonds in such compounds are in the form of (meth)acryloyl groups. (Meth)acryloyl and (meth)acryl, here and in the following, denote acryloyl and/or methacryloyl, and acryl and/or methacryl, respectively. Preferably at least two polymerizable double bonds in the form of (meth)acryloyl groups are present in the molecule. The compounds may be, for example, (meth)acryloyl-functional oligomeric and/or polymeric compounds of poly(meth)acrylate. The number average molecular weight of such a compound may be, for example, from 300 to 10 000, preferably from 800 to 10 000. The compounds containing preferably free-radical-polymerizable double bonds in the form of (meth)acryloyl groups can be obtained according to customary methods, for example by reaction of poly(meth)acrylates with (meth) acrylic acid. That method, and further methods of preparation, are described in the literature and are known to the person skilled in the art. Such unsaturated oligomers can also be termed prepolymers.

Functional Polymers:

As component (A) it is also possible to use unsaturated acrylates having reactive functional groups. The reactive functional group can, e.g.; be selected from hydroxyl, thiol, isocyanate, epoxy, anhydride, carboxyl, amino and blocked amino groups. Examples of OH-group-containing unsaturated acrylates are hydroxyethyl acrylates, hydroxybutyl acrylates and also glycidyl acrylates.

Examples of suitable monomers normally used to form the backbone (the base polymer) of such functionalized acrylate and methacrylate polymers include, for example, acrylate, methyl acrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate etc.. In addition, suitable amounts of functional monomers are copolymerized during the polymerization in order to obtain the functional polymers in that manner. Acid-functionalized acrylate or methacrylate polymers are obtained using acid-functional monomers, such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate, 3,4-dihydroxybutyl methacrylate, or from acrylates derived from glycerol derivatives.

Epoxy-functionalized acrylate or methacrylate polymers are obtained using epoxy-functional monomers, such as glycidyl methacrylate, 2,3-epoxybutyl methacrylate, 3,4-epoxybutyl methacrylate, 2,3-epoxycyclohexyl methacrylate, 10,11-epoxyundecyl methacrylate etc.. Similarly, it is possible, for example, for isocyanate-functionalized polymers to be prepared from isocyanate-functionalized monomers, for example meta-isopropenyl-α,α-dimethylbenzyl isocyanate. Amino-functionalized polymers include, for example, polyacrylamides. Nitrile-group-containing polymers include, for example, polyacrylonitriles.

Esters

There are especially suitable, for example, esters of ethylenically unsaturated mono- or polyfunctional carboxylic acids and polyols or polyepoxides, and polymers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acryl groups in side chains, and also mixtures of one or more such polymers.

Examples of suitable mono- or poly-functional unsaturated carboxylic acids are acrylic acid, methacrylic acid, crotonic acid, itaconic acid, cinnamic acid, maleic acid, fumaric acid, itaconic acid, and unsaturated fatty acids such as linolenic acid or oleic acid. Acrylic acid and methacrylic acid are preferred.

It is also possible, however, for saturated di- or poly-carboxylic acids to be used in admixture with unsaturated carboxylic acids. Examples of suitable saturated di- or polycarboxylic acids include, for example, tetrachlorophthalic acid, tetrabromophthalic acid, phthalic anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid etc..

Suitable polyols are aromatic and especially aliphatic and cycloaliphatic polyols. Examples of aromatic polyols include hydroquinone, 4,4'-dihydroxydiphenyl, 2,2-di(4-hydroxyphenyl)-propane, and novolaks and resols. Examples of polyepoxides are those based on the said polyols, especially the aromatic polyols, and epichlorohydrin. Also suitable as polyols are polymers and copolymers that contain hydroxyl groups in the polymer chain or in side groups, e.g. polyvinyl alcohol and copolymers thereof and polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- and 1,3-propanediol, 1,2-, 1,3- and 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- and 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified with one or with different unsaturated carboxylic acid(s), it being possible for the free hydroxyl groups in partial esters to be modified, for example etherified, or esterified with other carboxylic acids.

Examples of esters are:

trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, penta-erythritol triacrylate, pentaerythritol tetraacrylate, dipentaerythritol diacrylate, dipenta-erythritol triacrylate, dipentaerythritol tetraacrylate, dipentaerythritol pentaacrylate, dipenta-erythritol hexaacrylate, tripentaerythritol octaacrylate, pentaerythritol dimethacrylate, penta-erythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

The following esters are also suitable: dipropylene glycol diacrylate, tripropylene glycol diacrylate, 1,6-hexanediol diacrylate, glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Amides

Also suitable as component (A) are the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2- and 1,3-propylenediamine, 1,2-, 1,3- and 1,4-butylenediamine, 1,5-pentylenediamine, 1,6-hexylenediamine, octylenediamine, dodecylenediamine, 1,4-diaminocyclohexane, isophorone diamine, phenylenediamine, bisphenylenediamine, di-β-aminoethyl ether, diethylenetriamine, triethylenetetramine and di(β-aminoethoxy)- and di(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine tris-methacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They may be used together with ethylenically unsaturated comonomers, e.g. styrene. The polyesters and polyamides may also be derived from dicarboxylic acids and ethylenically unsaturated diols or diamines, especially from those having relatively long chains of e.g. from 6 to 20 carbon atoms. Examples of polyurethanes are those composed of saturated diisocyanates and unsaturated diols or unsaturated diisocyanates and saturated diols.

Aminoacrylates Especially Suitable as Component (A)

There are especially suitable as component (A) acrylates that have been modified by reaction with primary or secondary amines, as is described, e.g., in U.S. Pat. No. 3,844,916 by Gaske, in EP 280 222 by Weiss et al., in U.S. Pat. No. 5,482,649 by Meixner et al. or in U.S. Pat. No. 5,734,002 by Reich et al. Such amine-modified acrylates are also referred to as aminoacrylates. Aminoacrylates are obtainable, for example, from UCB Chemicals under the names EBECRYL 80, EBECRYL 81, EBECRYL 83 and EBECRYL 7100, from BASF under the names Laromer PO 83F, Laromer PO 84F and Laromer PO 94F, from Cognis under the names PHOTOMER 4775 F and PHOTOMER 4967 F, or from Cray Valley under the names CN501, CN503 and CN550.

The photopolymerisable compounds (A) can be used on their own or in any desired mixture.

Component (C)

The following are examples of special binders suitable as component (C):

1. surface coatings based on cold- or hot-crosslinkable alkyd, acrylate, polyester, epoxy or melamine resins or mixtures of such resins, optionally with the addition of a curing catalyst;
2. two-component polyurethane surface coatings based on hydroxyl-group-containing acrylate, polyester or polyether resins and aliphatic or aromatic isocyanates, isocyanurates or polyisocyanates;
3. two-component polyurethane surface coatings based on thiol-group-containing acrylate, polyester or polyether resins and aliphatic or aromatic isocyanates, isocyanurates or polyisocyanates;
4. one-component polyurethane surface coatings based on blocked isocyanates, isocyanurates or polyisocyanates which are deblocked during stoving; the addition of melamine resins is also possible, if desired;
5. one-component polyurethane surface coatings based on aliphatic or aromatic urethanes or polyurethanes and hydroxyl-group-containing acrylate, polyester or polyether resins;
6. one-component polyurethane surface coatings based on aliphatic or aromatic urethane acrylates or polyurethane acrylates having free amine groups in the urethane structure and melamine resins or polyether resins, optionally with the addition of a curing catalyst;
7. two-component surface coatings based on (poly)ketimines and aliphatic or aromatic isocyanates, isocyanurates or polyisocyanates;
8. two-component surface coatings based on (poly)ketimines and an unsaturated acrylate resin or a polyacetoacetate resin or a methacrylamidoglycolate methyl ester;
9. two-component surface coatings based on carboxyl- or amino-group-containing polyacrylates and polyepoxides;
10. two-component surface coatings based on anhydride-group-containing acrylate resins and a polyhydroxy or polyamino component;
11. two-component surface coatings based on acrylate-containing anhydrides and poly-epoxides;
12. two-component surface coatings based on (poly)oxazolines and anhydride-group-containing acrylate resins or unsaturated acrylate resins or aliphatic or aromatic isocyanates, isocyanurates or polyisocyanates;
13. two-component surface coatings based on unsaturated (poly)acrylates and (poly)-malonates;
14. thermoplastic polyacrylate surface coatings based on thermoplastic acrylate resins or extrinsically crosslinking acrylate resins in combination with etherified melamine resins;
15. surface-coating systems, especially clearcoats, based on malonate-blocked isocyanates with melamine resins (e.g. hexamethoxymethylmelamine) as crosslinkers (acid-catalysed);
16. UV-curable systems based on oligomeric urethane acrylates and/or acylate acrylates, optionally with the addition of other oligomers or monomers;
17. dual-cure systems, which are cured first thermally and then by UV, or vice versa, the constituents of the surface-coating formulation containing double bonds that can be caused to react by UV light and photoinitiators and/or by electron-beam curing.

Further Additives (C)

Depending on the intended application, the photopolymerizable mixtures may also, where appropriate, comprise further customary additives (C) in addition to the photoinitiator.

Examples thereof are:

antioxidants, optical brighteners, fillers, thermal inhibitors, which are intended to prevent premature polymerization, e.g. 2,2,6,6-tetramethyl-4-hydroxypiperidin-1-oxyl (4-hydroxy-TEMPO) and derivatives thereof;

antistatics, wetting agents or flow improvers and adhesion promoters;

thermally drying or curing catalysts, e.g. organometal compounds, amines or/and phosphines;

UV absorbers and light stabilisers, for example those from the group of the 2-(2'-hydroxyphenyl)-benzotriazoles, the 2-hydroxybenzophenones, esters of unsubstituted or substituted benzoic acids, acrylates, sterically hindered amines, oxalic acid diamides, 2-(2-hydroxyphenyl)-1,3,5-triazines, phosphites and phosphonites.

The following are examples of antioxidants, light stabilisers, UV absorbers and optical brighteners: ®IRGANOX 1035, 1010, 1076, 1222, ®TINUVIN P, 234, 320, 326, 327, 328, 329, 213, 292, 144, 622LD (available commercially from Ciba Specialty Chemicals), ®ANTIGENE P, 3C, FR, GA-80, ®SUMISORB TM-061 (available commercially from Sumitomo Chemical Industries Co.), ®SEESORB 102, 103, 501, 202, 712, 704 (available commercially from Sypro Chemical Co., Ltd.), ®SANOL LS770 (available commercially from Sankyo Co. Ltd.) ®UVITEX OB, available commercially from Ciba Specialty Chemicals. Combined additives of sterically hindered piperidine derivatives (HALS) and sterically hindered phenols, for example additives of IRGANOX 1035 and TINUVIN 292, for example in a weight ratio of 1:1, are especially advantageous.

The photopolymerization may furthermore be accelerated by adding, as further additives (C), photosensitizers which shift or broaden the spectral sensitivity. Such photosensitizers are especially aromatic carbonyl compounds, such as benzophenone derivatives, thioxanthone derivatives, including especially isopropylthioxanthone, anthraquinone derivatives and 3-acylcoumarin derivatives, terphenyls, styryl ketones, and also 3-(aroylmethylene)-thiazolines, camphorquinone, and also eosine dyes, rhodamine dyes and erythrosine dyes.

The formulations may also comprise dyes and/or white or coloured pigments. Depending on the intended application, both inorganic and organic pigments may be used.

The above-described additives (C) are customary in the art and are accordingly used in the amounts customary in the art.

It is also possible to add solvents or water to the compositions used in the process of the invention. Suitable solvents are solvents that are known to the person skilled in the art, especially those customary in surface-coatings technology. Radiation-curable aqueous prepolymer dispersions are available commercially in many variations. Such a dispersion is to be understood as consisting of water and at least one prepolymer dispersed therein.

Further Photoinitiators (D)

It will be understood that it is also possible to use mixtures with known photoinitiators (D), e.g.

Benzophenones of the Formula

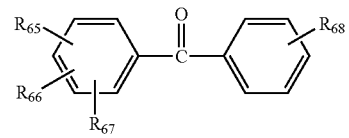

wherein $R_{65}$, $R_{66}$ and $R_{67}$ independently of one another are hydrogen, $C_1$-$C_4$-alkyl, $C_1$-$C_4$-halogenalkyl, $C_1$-$C_4$-alkoxy, chlorine or $N(C_1$-$C_4$-alkyl$)_2$;

$R_{68}$ is hydrogen, $C_1$-$C_4$-alkyl, $C_1$-$C_4$-halogenalkyl, phenyl, $N(C_1$-$C_4$-alkyl$)_2$, $COOCH_3$,

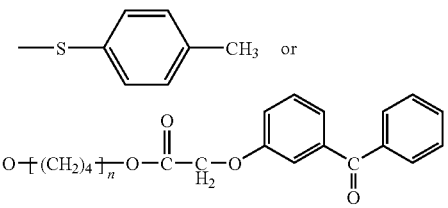

with n being 2-10.

Examples are:

ESACURE TZT® available from Lamberti, (a mixture of 2,4,6-trimethylbenzophenone and 4-methylbenzophenone).

Benzophenone, Darocur® BP

Alpha-Hydroxyketones, Alpha-Alkoxyketones or Alpha-Aminoketones of the Formula

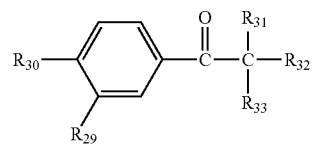

wherein $R_{29}$ is hydrogen or $C_1$-$C_{18}$-alkoxy;

$R_{30}$ is hydrogen, $C_1$-$C_{18}$-alkyl, $C_1$-$C_{18}$-alkoxy, —$OCH_2CH_2$—$OR_{47}$, morpholino, $SCH_3$, a group

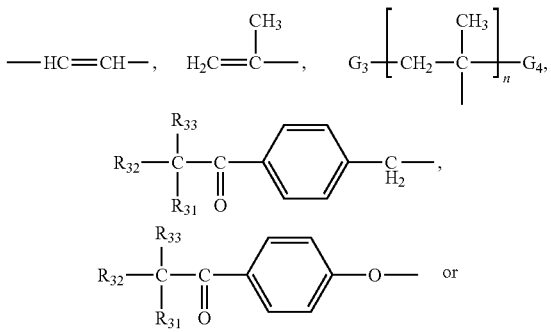

-continued

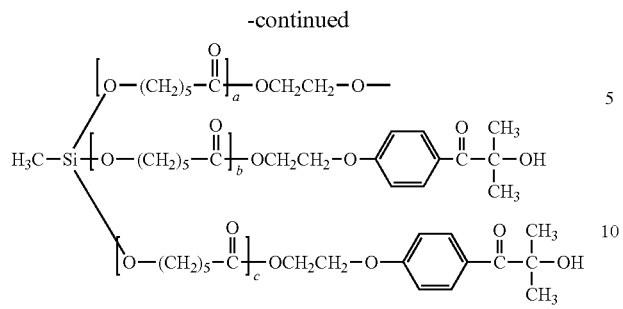

a, b and c are 1-3;

n is 2-10;

$G_3$ and $G_4$ independently of one another are end groups of the polymeric structure, preferably hydrogen or methyl;

$R_{47}$ is hydrogen,

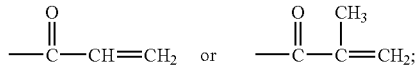

$R_{31}$ is hydroxy, $C_1$-$C_{16}$-alkoxy, morpholino, dimethylamino or —O(CH$_2$CH$_2$O)$_m$—$C_1$-$C_{16}$-alkyl;

$R_{32}$ and $R_{33}$ independently of one another are hydrogen, $C_1$-$C_6$-alkyl, $C_1$-$C_{16}$-alkoxy or —O(CH$_2$CH$_2$O)$_m$—$C_1$-$C_{16}$-alkyl; or unsubstituted phenyl or benzyl; or phenyl or benzyl substituted by $C_1$-$C_{12}$-alkyl; or $R_{32}$ and $R_{33}$ together with the carbon atom to which they are attached form a cyclohexyl ring; m is 1-20;

with the proviso that $R_{31}$, $R_{32}$ and $R_{33}$ are not simultaneously $C_1$-$C_{16}$-alkoxy or —O(CH$_2$CH$_2$O)$_m$—$C_1$-$C_{16}$-alkyl.

Examples are:

1-Hydroxy-cyclohexyl-phenyl-ketone (IRGACURE®184) or IRGACUR®500 (a mixture of IRGACURE®184 with benzophenone);

2-Methyl-1[4-(methylthio)phenyl]-2-morpholinopropan-1-one; (IRGACURE®907)

2-Benzyl-2-dimethylamino-1-(4-morpholinophenyl)-butanone-1; (IRGACURE®369)

1-[4-(2-Hydroxyethoxy)-phenyl]-2-hydroxy-2-methyl-1-propan-1-one; (IRGACURE®2959)

2,2-Dimethoxy-1,2-diphenylethan-1-one (IRGACURE®651)

2-Hydroxy-2-methyl-1-phenyl-propan-1-one; (DAROCUR®1173)

2-Dimethylamino-2-(4-methyl-benzyl)-1-(4-morpholin-4-yl-phenyl)-butan-1-one;

2-Benzyl-1-(3,4-dimethoxy-phenyl)-2-dimethylamino-butan-1-one;

2-Hydroxy-1-{4-[4-(2-hydroxy-2-methyl-propionyl)-benzyl]-phenyl}-2-methyl-propan-1-one;

2-Hydroxy-1-{4-[4-(2-hydroxy-2-methyl-propionyl)-phenoxy]-phenyl}-2-methyl-propan-1-one, Another example of an alpha-hydroxy ketone is a compound of the formula

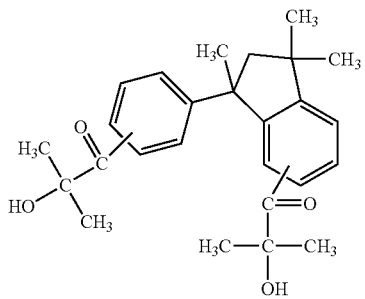

for example ESACURE KIP from Fratelli Lamberti, 2-hydroxy-1-{1-[4-(2-hydroxy-2-methyl-propionyl)-phenyl]-1,3,3-trimethyl-indan-5-yl}-2-methyl-propan-1-one.

Irgacure and Darocur products are available from Ciba Specialty Chemicals Inc.

Acylphosphine Oxides of the Formula

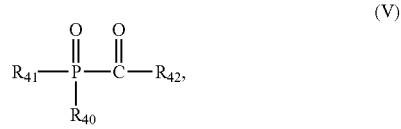

wherein $R_{40}$ and $R_{41}$ independently of one another are unsubstituted $C_1$-$C_{20}$-alkyl, cyclohexyl, cyclopentyl, phenyl, naphthyl or biphenylyl; or $C_1$-$C_{20}$-alkyl, cyclohexyl, cyclopentyl, phenyl, naphthyl or biphenylyl substituted by halogen, $C_1$-$C_{12}$-alkyl, $C_1$-$C_{12}$-alkoxy, $C_1$-$C_{12}$alkylthio or by $NR_{52}R_{53}$, or $R_{40}$ and $R_{41}$ are independently of one another —(CO)$R_{42}$; wherein $R_{52}$ and $R_{53}$ independently of one another are hydrogen, unsubstituted $C_1$-$C_{12}$-alkyl or $C_1$-$C_{12}$-alkyl substituted by OH or by SH wherein the alkyl chain may be interrupted by one to four oxygen atoms; or $R_{52}$ and $R_{53}$ independently of one another are $C_2$-$C_{12}$-alkenyl, cyclopentyl, cyclohexyl, benzyl or phenyl;

$R_{42}$ is unsubstituted cyclohexyl, cyclopentyl, phenyl, naphthyl or biphenylyl, or cyclohexyl, cyclopentyl, phenyl, naphthyl or biphenylyl substituted by halogen, $C_1$-$C_4$-alkyl and/or $C_1$-$C_4$-alkoxy; or $R_{42}$ is a 5- or 6-membered heterocyclic ring having an S atom or N atom;

Examples are:

bis(2,4,6-trimethylbenzoyl)-phenylphosphine oxide; IRGACUR®819

2,4,6-trimethylbenzoyl-diphenyl-phosphine oxide; Darocur® TPO bis(2,6-dimethoxybenzoyl)-2,4,4-trimethylpentylphosphine oxide.

Titanocenes of the Formula

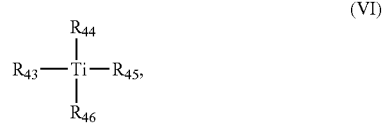

wherein $R_{43}$ and $R_{44}$ independently of one another are cyclopentadienyl optionally mono-, di-, or tri-substituted by $C_1$-$C_{18}$-alkyl, $C_1$-$C_{18}$-alkoxy, cyclopentyl, cyclohexyl or by halogen;

$R_{45}$, and $R_{46}$ are phenyl having at least one F or $CF_3$ substituent in ortho position to the Ti—C bond and having at least a further substituent which is unsubstituted pyrrolinyl or polyoxaalkyl or which is pyrrolinyl or polyoxaalkyl substituted by one or two $C_1$-$C_{12}$-alkyl, di($C_1$-$C_{12}$-alkyl)aminomethyl, morpholinomethyl, $C_2$-$C_4$-alkenyl, methoxymethyl, ethoxymethyl, trimethylsilyl, formyl, methoxy or phenyl groups; or $R_{45}$ and $R_{46}$ are

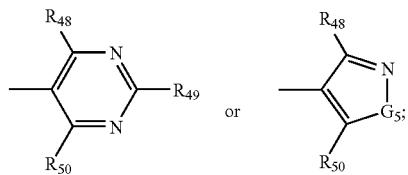

wherein $G_5$ is O, S, or $NR_{51}$ with $R_{51}$ being $C_1$-$C_8$alkyl, phenyl or cyclophenyl;

$R_{48}$, $R_{49}$ and $R_{50}$ independently of one another are hydrogen, halogen, $C_2$-$C_{12}$-alkenyl, $C_1$-$C_{12}$alkoxy; $C_2$-$C_{12}$-alkoxy interrupted by one to four oxygen atoms; cyclohexyloxy, cyclopentyloxy, phenoxy, benzyloxy, unsubstituted phenyl or biphenyl or phenyl or biphenyl substituted by $C_1$-$C_4$-alkoxy, halogen, phenylthio or by $C_1$-$C_4$-alkylthio, with the proviso that $R_{48}$ and $R_{50}$ are not both hydrogen and that with respect to the residue

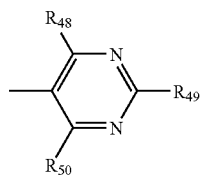

at least one substituent $R_{48}$ or $R_{50}$ is $C_1$-$C_{12}$alkoxy or $C_1$-$C_{12}$alkoxy interrupted by one to four oxygen atoms, or is cyclohexyloxy, cyclopentyloxy, phenoxy or benzyloxy.

Examples are:

Bis(.eta.5-2,4-cyclopentadien-1-yl)-bis(2,6-difluoro-3-(1H-pyrrol-1-yl)-phenyl)-titanium IRGACURE® 784

Bis(2,6-difluorophenyl)bis[(1,2,3,4,5-eta)-1-methyl-2,4-cyclopentadien-1-yl]-titanium IRGACURE® 727

Phenylglyoxalates of the Formula

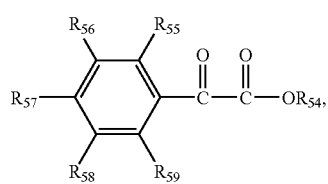

(VII)

wherein $R_{54}$ is hydrogen, $C_1$-$C_{12}$-alkyl or a group

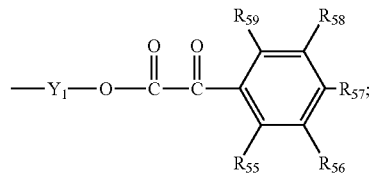

$R_{55}$, $R_{56}$, $R_{57}$, $R_{58}$, and $R_{59}$ independently of one another are hydrogen, unsubstituted $C_1$-$C_{12}$-alkyl or $C_1$-$C_{12}$-alkyl substituted by OH, $C_1$-$C_4$-alkoxy, phenyl, naphthyl, halogen or by CN; and wherein the alkyl chain may be interrupted by one or more oxygen atoms; or $R_{55}$, $R_{56}$, $R_{57}$, $R_{58}$ and $R_{59}$ independently of one another are $C_1$-$C_4$-alkoxy, $C_1$-$C_4$-alkylthio or $NR_{52}R_{53}$;

$R_{52}$ and $R_{53}$ independently of one another are hydrogen, unsubstituted $C_1$-$C_{12}$-alkyl or $C_1$-$C_{12}$-alkyl substituted by OH or by SH wherein the alkyl chain may be interrupted by one to four oxygen atoms; or $R_{52}$ and $R_{53}$ independently of one another are $C_2$-$C_{12}$-alkenyl, cyclopentyl, cyclohexyl, benzyl or phenyl.

$Y_1$ is $C_1$-$C_{12}$-alkylene optionally interrupted by one or more oxygen atoms.

An example is oxo-phenyl-acetic acid 2-[2-(2-oxo-2-phenyl-acetoxy)-ethoxy]-ethyl ester.

Surface-Active Photoinitiators

Surface-active benzophenones as described in WO 02/48204 of the formula

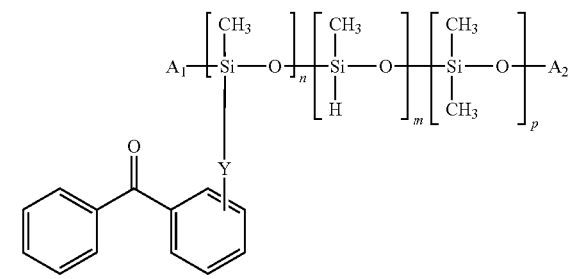

wherein $A_1$ is methyl or —O—Si(CH$_3$)$_3$ $A_2$ is methyl or —Si(CH$_3$)$_3$;

Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—; wherein the oxygen is attached to the benzene ring;

a and b are independently of one another 1-10;

n is a number from 1 to 10;

m is a number from 0 to 25;

p is a number from 0 to 25.

An example is

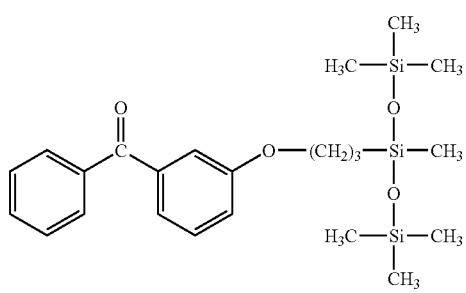

Siloxane-Modified Hydroxyketones as Described in EP 1072326

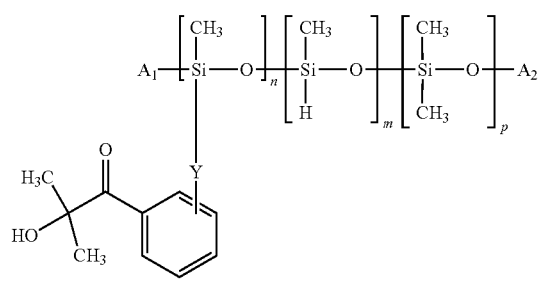

wherein
A$_1$ is methyl or —O—Si(CHO$_3$)$_3$
A$_2$ is methyl or —Si(CH$_3$)$_3$;
Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—; wherein the oxygen is attached to the benzene ring;
a and b are independently of one another 1-10;
n is a number from 1 to 10;
m is a number from 0 to 25;
p is a number from 0 to 25.

An example is

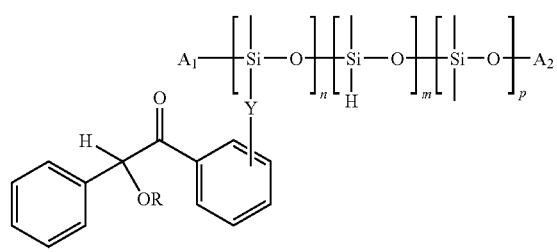

Surface-active Benzil Dialkyl Ketals (BDK) or Benzoins as Described in WO 02/48203

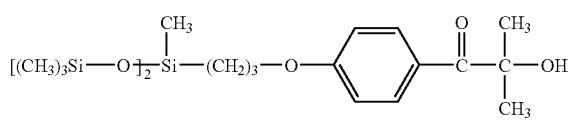

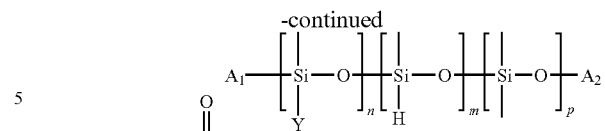

wherein
R is H or C$_1$-C$_4$alkyl;
A$_1$ is methyl or —O—Si(CH$_3$)$_3$
A$_2$ is methyl or —Si(CH$_3$)$_3$;
Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—; wherein the oxygen is attached to the benzene ring;
a and b are independently of one another 1-10;
n is a number from 1 to 10;
m is a number from 0 to 25;
p is a number from 0 to 25.

Examples are

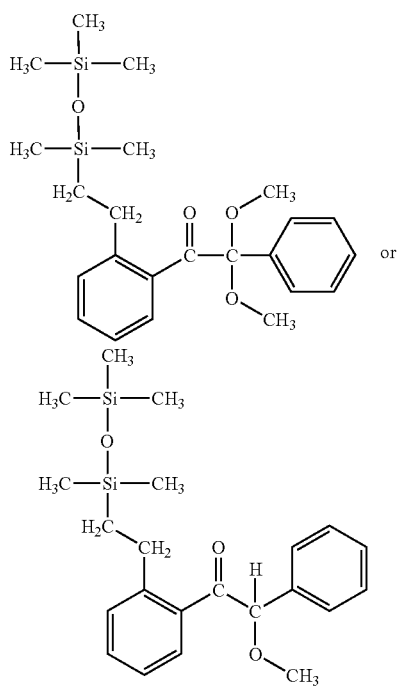

Monomeric and Dimeric Arylglyoxalic Acid Esters Modified with Siloxane via an Ester Group as Described in WO 02/14439

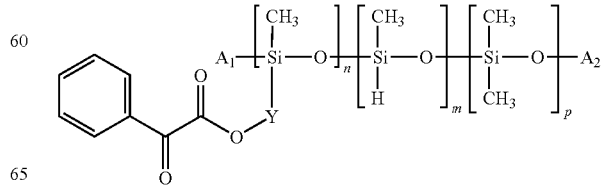

wherein

A$_1$ is methyl or —O—Si(CH$_3$)$_3$

A$_2$ is methyl or Si(CH$_3$)$_3$;

Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—; wherein the oxygen is attached to the benzene ring;

a and b are independently of one another 1-10;

n is a number from 1 to 10;

m is a number from 0 to 25;

p is a number from 0 to 25.

An example is

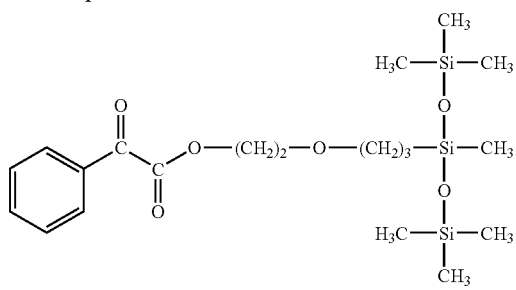

Monomeric and Dimeric Arylglyoxalic Acid Esters Modified with Siloxane via an Aromatic Group as Described in WO 02/14326

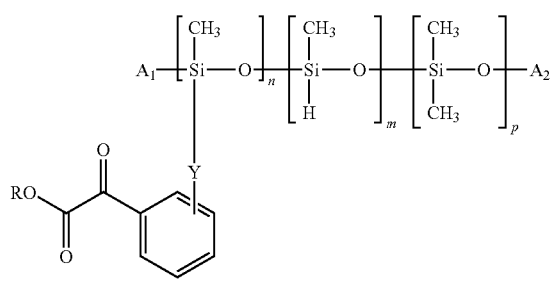

wherein

R is C$_1$-C$_4$alkyl;

A$_1$ is methyl or —O—Si(CH$_3$)$_3$

A$_2$ is methyl or —Si(CH$_3$)$_3$;

Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—; wherein the oxygen is attached to the benzene ring;

a and b are independently of one another 1-10;

n is a number from 1 to 10;

m is a number from 0 to 25;

p is a number from 0 to 25.

An example is

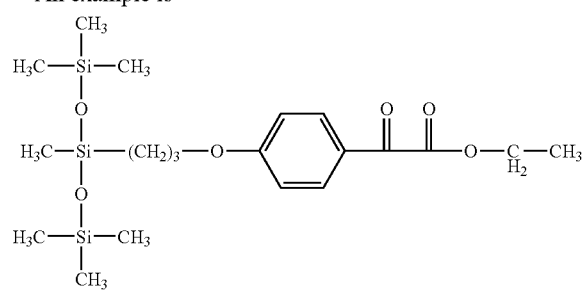

Long-chain-alkyl-modified hydroxyketones as described in WO 02/48202, for example 1-(4-docosyloxy-phenyl)-2-hydroxy-2-methyl-1-propanone

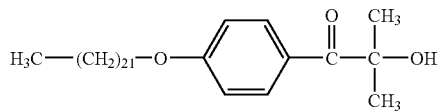

A further example of a photoinitiator is Esacure 1001 available from Lamberti:

1-[4-(4-benzoylphenylsulfanyl)phenyl]-2-methyl-2-(4-methylphenylsulfonyl)propan-1-one

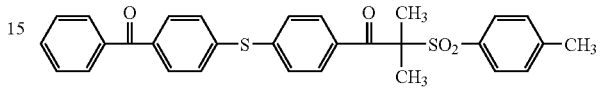

It is also possible to add cationic photoinitiators, such as benzoyl peroxide (other suitable peroxides are described in U.S. Pat. No. 4,950,581, column 19, lines 17-25), or aromatic sulfonium, phosphonium or iodonium salts, such as are described, for example, in U.S. Pat. No. 4,950,581, column 18, line 60 to column 19, line 10.

An example of an iodonium salt is (4-isobutyl-phenyl)-4-methylphenyl-iodonium hexafluoro-phosphate.

Maleimide derivatives may also be present, as described, e.g., in U.S. 6,153,662 or U.S. Pat. No. 6,150,431 by First Chemicals. N-(2-Trifluoromethylphenyl)maleimide and N-(2-tert-butylphenyl)maleimide may be mentioned by way of example.

The following may also be present: camphorquinones, acetophenones, 4-aroyl-1,3-dioxolanes, benzoin alkyl ethers and benzil ketals, e.g. benzil dimethyl ketal, peresters, e.g. benzophenonetetracarboxylic acid perester as described e.g. in EP 126 541; halomethyltriazines, e.g. 2-[2-(4-methoxyphenyl)-vinyl]-4,6-bistrichloromethyl[1,3,5]triazine, 2-(4-methoxyphenyl)-4,6-bistrichloromethyl-[1,3,5]triazine, 2-(3,4-dimethoxyphenyl)-4,6-bistrichloromethyl[1,3,5]triazine or 2-methyl-4,6-bistrichloromethyl[1,3,5]triazine, hexaarylbisimidazole/coinitiator systems, e.g. ortho-chlorohexaphenyl bisimidazole together with 2-mercaptobenzothiazole, ferrocenium compounds or borate photoinitiators.

The photopolymerizable compositions contain the photoinitiator advantageously in an amount of from 0.05 to 15% by weight, preferably from 0.5 to 10% by weight, based on the composition. The stated amount of photoinitiator relates to the sum of all of the photo-initiators added when mixtures thereof are used, i.e. either to the photoinitiator (B) or to the photoinitiators (B)+(D).

Use

The photocurable compositions according to the invention are suitable for a variety of purposes, for example for overprint coatings, for inkjet inks, for printing inks, especially flexographic printing inks, for clearcoats, whitecoats or color-pigmented paint, for example for wood or metal, for powder coatings, as coating materials for substrates of all kinds, e.g. wood, textiles, paper, ceramics, glass, glass fibres, plastics, such as polyesters, polyethylene terephthalate, polyolefins or cellulose acetate, especially in the form of films, and also for metals, such as Al, Cu, Ni, Fe, Zn, Mg or Co and GaAs, Si or SiO$_2$, to which a protective coating is to be applied or an image is to be applied by imagewise exposure. Examples of coatings for metal include the application of a finish to metal sheets and tubes, cans or bottle closures, and topcoats for applications in the automobile industry Examples of the photocuring of paper coatings are the application of a colourless finish to labels or book covers.

The photopolymerisable compositions can furthermore be used as daylight-curable paints for marking structures and roads, for photographic reproduction techniques, for holographic recording materials, for image recording processes or in the production of printing plates that can be developed using organic solvents or using aqueous alkaline media, for the production of masks for screen printing, as dental filling compounds, as adhesives, as pressure-sensitive adhesives, as laminating resins, as etch resists or permanent resists, both liquid and in the form of dry films, as photostructurable dielectrics, and as solder resists for electronic circuits, as resists in the production of color filters for any type of display screen, or in the creation of structures during the production of plasma displays and electroluminescent displays, in the production of optical switches, optical gratings (interference gratings), in the production of three-dimensional articles by bulk curing (UV curing in transparent moulds) or by the stereolithography process, as described, for example, in U.S. Pat. No. 4,575,330, in the production of composite materials (e.g. styrene polyesters which may, where appropriate, include glass fibres and/or other fibres and other adjuvants), and of fine layers (gel coats) and thick-layered compositions, in the coating or sealing of electronic components, or as coatings for optical fibres. The compositions are suitable, furthermore, for the production of optical lenses, e.g. contact lenses or Fresnel lenses, and also for the production of medical instruments, aids or implants.

The compositions may also be used to produce gels having thermotropic properties, such as are described, for example, in DE 197 00 064 and EP 678 534.

A preferred area of use is in overprint coatings. Typically, these consist of ethylenically unsaturated compounds, such as oligomeric and/or monomeric acrylates and aminoacrylates. Suitable compounds are listed under "compound (A)". The compounds and mixtures according to the invention are especially effective in overprint coatings of small layer thickness (5-10 µm).

A further preferred area of use is in UV-curable flexographic printing inks. Such inks likewise consist of ethylenically unsaturated compounds (A) and comprise in addition UV flexographic resin/binder as well as further additives, such as flow agents and coloured pigments.

A further preferred area of use is in powder coatings. The powder coatings may be based on solid resins and monomers containing reactive double bonds (compounds (A)), e.g. maleates, vinyl ethers, acrylates, acrylamides and mixtures thereof. The powder coatings may also comprise binders, such as are described, for example, in DE 4 228 514 and EP 636 669. The UV-curable powder coatings may also comprise white or coloured pigments.

A further preferred area of use is in inkjet inks.

Inkjet inks contain a colorant.

A wide variety of organic and inorganic dyes and pigments, alone or in combination, may be selected for use in the inkjet ink compositions of this invention. The pigment particles should be sufficiently small (0.005 to 15 µm) to permit free flow of the ink at the ejecting nozzles. The pigment particles should preferably be 0.005 to 1 µm.

Very fine dispersions of pigments and their preparation are disclosed in e.g. U.S. Pat. No. 5,538,548.

The pigment can be black, white, cyan, magenta, yellow, red, blue, green, brown, mixtures thereof, and the like. For example, suitable pigment materials include carbon blacks such as Regal 400R, Mogul L, Elftex 320 from Cabot Colo., or Carbon Black FW18, Special Black 250, Special Black 350, Special Black 550, Printex 25, Printex 35, Printex 55, Printex 150T from Degussa Colo., and Pigment Black 7. Additional examples of suitable pigments are disclosed in, for example, U.S. Pat. No. 5,389,133.

Suitable white pigments are titanium dioxide (modifications rutile and anatas), e.g. KRONOS 2063 from Kronos, or HOMBITAN R610 L from Sachtleben.

Suitable pigments include, for instance, C. I. Pigment Yellow 17, C. I. Pigment Blue 27, C. I. Pigment Red 49:2, C. I. Pigment Red 81:1, C. I. Pigment Red 81:3, C. I. Pigment Red 81:x, C. I. Pigment Yellow 83, C. I. Pigment Red 57:1, C. I. Pigment Red 49:1, C. I. Pigment Violet 23, C. I. Pigment Green 7, C. I. Pigment Blue 61, C. I. Pigment Red 48:1, C. I. Pigment Red 52:1, C. I. Pigment Violet 1, C. I. Pigment White 6, C. I. Pigment Blue 15, C. I. Pigment Yellow 12, C. I. Pigment Blue 56, C. I. Pigment Orange 5, C. I. Pigment Black 7, C. I. Pigment Yellow 14, C. I. Pigment Red 48:2, C. I. Pigment Blue 15:3, C. I. Pigment Yellow 1, C. I. Pigment Yellow 3, C. I. Pigment Yellow 13, C. I. Pigment Orange 16, C. I. Pigment Yellow 55, C. I. Pigment Red 41, C. I. Pigment Orange 34, C. I. Pigment Blue 62, C. I. Pigment Red 22, C. I. Pigment Red 170, C. I. Pigment Red 88, C. I. Pigment Yellow 151, C. I. Pigment Red 184, C. I. Pigment Blue 1:2, C. I. Pigment Red 3, C. I. Pigment Blue 15:1, C.I. Pigment Blue 15:3, C.I. Pigment Blue 15:4, C. I. Pigment Red 23, C. I. Pigment Red 112, C. I. Pigment Yellow 126, C. I. Pigment Red 169, C. I. Pigment Orange 13, C. I. Pigment Red 1-10, 12, C.I. Pigment Blue 1:X, C.I. Pigment Yellow 42, C.I. Pigment Red 101, C.I. Pigment Brown 6, C. I. Pigment Brown 7, C. I. Pigment Brown 7:X, C. I. Pigment Black 11, C. I. Pigment Metal 1, C. I. Pigment Metal 2, C.I. Pigment Yellow 128, C.I. Pigment Yellow 93, C.I. Pigment Yellow 74, C.I. Pigment Yellow 138, C.I. Pigment Yellow 139, C.I. Pigment Yellow 154, C. I. Pigment Yellow 185, C.I. Pigment Yellow 180, C.I. Pigment Red 122, C.I. Pigment Red 184, and bridged aluminum phtalocyanine pigments, C. I. Pigment Red 254, C. I. Pigment Red 255, C.I. Pigment Red 264, C. I. Pigment Red 270, C.I. Pigment Red 272, C. I. Pigment Violet 19, C.I. Pigment Red 166, C.I. Pigment Red 144C. I. Pigment Red 202, C. I. Pigment Yellow 110, C. I. Pigment Yellow 128, C. I. Pigment Yellow 150, C. I. Pigment Orange 71, C. I. Pigment Orange 64, C. I. Pigment Blue 60.

The pigment may, but need not, be in the form of a dispersion comprising a dispersant, also called pigment stabilizer. The latter may be, for example, of the polyester, polyurethane or polyacrylate type, especially in the form of a high molecular weight block copolymer, and would typically be incorporated at 2.5% to 100% by weight of the pigment. An example of a polyurethane dispersant is EFKA 4047.

Further pigment dispersions are (UNISPERSE, IRGASPERSE) and ORASOL Dyes (solvent soluble dyes): C.I. Solvent Yellow 146, C.I. Solvent Yellow 88, C.I. Solvent Yellow 89, C.I. Solvent Yellow 25, C.I. Solvent Orange 11, C.I. Solvent Orange 99, C.I. Solvent Brown 42, C.I. Solvent Brown 43, C.I. Solvent Brown 44, C.I. Solvent Red 130, C.I. Solvent Red 233, C.I. Solvent Red 125, C.I. Solvent Red 122, C.I. Solvent Red 127, C.I. Solvent Blue 136, C.I. Solvent Blue 67, C.I. Solvent Blue 70, C.I. Solvent Black 28, C.I. Solvent Black 29

Especially emphasized are the MICROLITH-pigment preparations commercially available from Ciba Specialty Chemicals Inc. These pigment dispersions may be organic or inorganic pigments predispersed in a variety of resins, e.g. in vinyl resins, acrylic resins and aromatic polyurethane resins. MICROLITH-WA may for example be a line of pigments predispersed in alkaline water/alcohol soluble acrylic resin (specially developed for aqueous gravure and flexographic printing) with pigments that may be compatible with UV and inkjet printing inks.

The Microlith-K inkjet products are used in vinyl-based inks, which can be formulated to give good adhesion to many substrates, ranging from plasticized and rigid PVC and metal foils, to polymer coated regenerated cellulose films.

Inkjet inks of the present invention may also more generally include other pigment preparations such as chips or in situ combination during grinding of pigments (as described above) and hyperdispersants (e.g. Solsperse as available from Avecia) into the binder carrier.

The substrates can be coated by applying a liquid composition, a solution or suspension to the substrate. The choice of solvent and the concentration are guided primarily by the nature of the composition and by the coating technique. The solvent should be inert, i.e. it should not enter into any chemical reaction with the components and it should be able to be removed again in the course of drying after coating. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxy-ethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating techniques, for example by spincoating, dipping, knife coating, curtain coating techniques, brush application, spraying, especially by electrostatic spraying, and reverse roll coating, and also by electrophoretic deposition. It is also possible to apply the photosensitive layer to a temporary flexible support and then to transfer the layer by lamination to the final substrate. Examples of methods of application can be found e.g. in Ullmann's Encyclopedia of Industrial Chemistry, 5$^{th}$ edition, Vol. A18, pp. 491-500.

The amount applied (layer thickness) and the nature of the substrate (layer support) are dependent on the desired field of application. The range of dry film thicknesses generally embraces values from about 0.1 μm to more than 100 μm.

The photosensitivity of the compositions of the invention generally ranges from about 200 nm into the NIR or IR region.

NIR (Near Infrared)-Curing

The NIR radiation used in the process according to the invention is short-wave infrared radiation in the wavelength range from about 750 nm to about 1500 nm, preferably 750 nm to 1200 nm. Radiation sources for NIR radiation include, for example, conventional NIR radiation emitters, which are available commercially (for example, from Adphos).

IR-Curing

The IR radiation used in the process according to the invention is medium-wave radiation in the wavelength range from about 1500 nm to about 3000 nm and/or longer-wave infrared radiation in the wavelength range above 3000 nm.

IR radiation emitters of this kind are available commercially (for example, from Heraeus).

UV-Curing

The photochemical curing step is carried out usually using light of wavelengths from about 200 nm to about 600 nm, especially from 200 to 450 nm. As light sources there are used a large number of the most varied types. Both point sources and planiform projectors (lamp carpets) are suitable. Examples are: carbon arc lamps, xenon arc lamps, medium-, high- and low-pressure mercury lamps, optionally doped with metal halides (metal halide lamps), microwave-excited metal-vapor lamps, excimer lamps, super actinic fluorescent tubes, fluorescent lamps, argon filament lamps, electronic flash lamps, photographic flood lights, electron beams and X-rays generated by means of synchrotrons or laser plasma.

As already mentioned, curing in the process of the invention may take place solely by exposure to electromagnetic radiation. Depending on the composition of the formulation to be cured, however, thermal curing before, during or after irradiation is advantageous.

Thermal curing takes place in accordance with methods known to the person skilled in the art. Curing is generally carried out in an oven, e.g. a circulating air oven, on a hotplate, or by irradiation using IR lamps. Curing without aids at room temperature is likewise possible, depending on the binder system used. The curing temperatures are generally from room temperature to 150° C., e.g. 25-150° C. or 50-150° C. In the case of powder coatings or "coil coat" coatings, the curing temperatures may also be higher, e.g. up to 350° C.

The invention relates also to a method of producing a scratch-resistant durable surface, wherein a composition that either contains an ethylenically unsaturated compound and a photoinitiator of formula I, or contains an ethylenically unsaturated compound with an aminoacrylate and also contains a photoinitiator of formula I, II, or III, is applied to a support; and curing of the formulation is carried out either solely by irradiation with electromagnetic radiation of a wavelength ranging from 200 nm into the NIR or IR region, or by irradiation with electromagnetic radiation and prior, simultaneous and/or subsequent action of heat.

The invention relates also to the use of the above-described composition and to a process for the production of pigmented and unpigmented surface coatings, overprint coatings, formulations for printing inks, inkjet inks, powder coatings, fine layers (gel coats), composite materials or glass fibre cable coatings.

The invention likewise relates to a coated substrate that has been coated on at least one surface with a composition as described above.

The following Examples further illustrate the invention:

EXAMPLE 1

Preparation of 2-hydroxy-1-{4-[4-(2-hydroxy-2-methyl-propionyl)-phenoxy]-phenyl}-2-methyl-propan-1-one

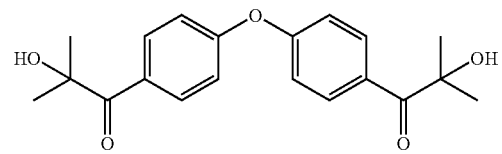

1) Friedel-Crafts Reaction 221.3 g (1.3 mol) of diphenyl ether, 318.6 g (2.99 mol) of isobutyric acid chloride and 300 ml of chlorobenzene are combined and cooled to from 5 to 0° C. using an ice-bath. 416.0 g (3.12 mol) of aluminium chloride are then added in small portions, in the course of approximately four hours, at an internal temperature of from 5 to 0° C. HCl gas is evolved. Stirring at an internal temperature of from 0 to 5° C. is then carried out for approximately 2 hours. At the end of that period all the aluminium chloride has dissolved. The dark-red reaction mixture is subsequently poured into ice and water and extracted by stirring. The two phases are separated in a separating funnel. The organic phase is washed with water and then concentrated at approximately 60° C. and approximately 25 mbar using a vacuum rotary evaporator. 436 g of a yellowish liquid which crystallises overnight are obtained. The crude product, bis[4-(2-methyl-propionyl)-phenyl] ether, melts at approximately 40-41° C. It still contains chlorobenzene. It is used in the next reaction without being further purified.

2) Enol Chlorination 218 g (0.65 mmol tq) of the crude product bis[4-(2-methyl-propionyl)-phenyl] ether from the Friedel-Crafts reaction are dissolved in 300 ml of glacial acetic acid and heated to from 55 to 60° C. using an oil bath. Then, at from 55 to 60° C. and while stirring well, 92.2 g (1.3 mol) of chlorine gas are introduced through a glass frit, relatively rapidly to begin with and only slowly at the end. The duration of the introduction is approximately 6 hours. The yellowish liquid is concentrated using a vacuum rotary evaporator. 249.5 g of yellowish oil which crystallises overnight are obtained. The crude product, bis[4-(2-chloro-2-methyl-propionyl)-phenyl] ether, melts at approximately 90-92° C. It still contains glacial acetic acid. It is used in the next reaction without being further purified.

3) Hydrolysis 208.0 g (1.56 mol) of 30% NaOH and 208 ml of deionised water and 205.7 g of methanol are combined. The temperature rises to approximately 36° C. The mixture is then heated to 50° C. using an oil bath. While stirring well, 249.5 g (0.65 mol tq) of the crude product bis[4-(2-chloro-2-methyl-propionyl)-phenyl] ether from the chlorination reaction, dissolved while warm with 230 ml of toluene and with 102.8 g of methanol, are then added dropwise in the course of approximately one hour. The internal temperature slowly rises to 55-60° C. The alkaline mixture (approximately pH 12) is then stirred for approximately from two to three hours at 55-60° C. The conversion is checked using a GC sample and using a $^1$H-NMR sample. The mixture is then cooled to 50° C. and adjusted to a pH of approximately 1-2 by the dropwise addition of approximately 68 g of 16% hydrochloric acid. The colour of the emulsion changes from a strong yellow to yellow. The mixture is subsequently stirred for approximately 30-60 minutes. When the hydrolysis is complete, the reaction mixture is rendered neutral with a small amount of dilute sodium hydroxide solution. The two phases are separated at approximately 50° C. in a separating funnel. 200 ml of water are added to the organic phase, which is stirred and separated off again. The warm organic phase is partially concentrated (approximately 100 ml) using a rotary evaporator in order to remove residual methanol and water. It is then diluted with 660 ml of warm toluene. The solution is seeded at 45° C. and is cooled later, after crystallisation. The thick suspension is filtered and washed with toluene. The white crystals, bis[4-(2-hydroxy-2-methyl-propionyl)-phenyl] ether, are dried in vacuo. 190.5 g of white crystals, which melt at 97.2-97.6° C., are obtained. In the $^1$H-NMR spectrum, the product 1,2-bis[4-(2-hydroxy-2-methyl-propionyl)-phenyl] ether is isomerically pure.

Elemental analysis: $C_{20}H_{22}O_5$

|  | % C |  | % H |
|---|---|---|---|
| calculated: | 70.16 | calculated: | 6.48 |
| found: | 69.95 | found: | 6.47 |

EXAMPLE 2

Preparation of 2-hydroxy-1-(4-{2-[4(2-hydroxy-2-methyl-propionyl)-phenyl]-ethyl}-phenyl)-2-methyl-propan-1-one

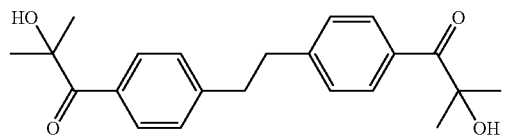

1) Friedel-Crafts Reaction 18.2 g (0.1 mol) of bibenzyl, 24.5 g (0.23 mol) of isobutyric acid chloride and 150 g of 1,2-dichlorobenzene are combined and cooled to from 5 to 0° C. using an ice-bath. 32.0 g (0.24 mol) of aluminium chloride are then added in small portions, in the course of approximately four hours, at an internal temperature of from 5 to 0° C. HCl gas is evolved. Stirring at an internal temperature of from 0 to 5° C. is then carried out for approximately 16 hours. At the end of that period all the aluminium chloride has dissolved. The reaction mixture is subsequently poured into ice and water and extracted by stirring. The two phases are separated in a separating funnel. The organic phase is washed with water and then concentrated using a vacuum rotary evaporator. 213.2 g of a yellowish liquid are obtained. The product, an isomeric mixture in which the chief component is 1,2-bis[4-(2-methyl-propionyl)-phenyl]-ethane, is used in the next reaction without being further purified. Found according to GC and $^1$H-NMR spectrum are 89% p,p isomer, 10% m,p isomer and 1% m,m isomer, without the solvent 1,2-dichlorobenzene.

2) Enol Chlorination 213.2 g (0.1 mol tq) of the solution of 1,2-bis[4-(2-methyl-propionyl)-phenyl]-ethane from the Friedel-Crafts reaction are heated to 55 to 60° C. using an oil bath. Then, at from 55 to 60° C. and while stirring well, 14.2 g (0.2 mol) of chlorine gas are introduced through a glass frit, relatively rapidly to begin with and only slowly at the end. The duration of the introduction is approximately 8 hours. 217.8 g of a colourless liquid are obtained. The product, a solution of 1,2-bis[4-(2-chloro-2-methyl-propionyl)-phenyl]ethane in 1,2-dichlorobenzene, is used in the next reaction without being further purified.

3) Epoxy Ether Preparation 19.8 g (0.11 mol) of 30% sodium methanolate solution in methanol are cooled to 10° C. In the course of approximately one hour, 108.9 g (0.05 mol tq) of the 1,2-dichlorobenzene solution of 1,2-bis[4-(2-chloro-2-methyl-propionyl)-phenyl]-ethane from the chlorination reaction, additionally diluted with 55 ml of methanol, are then added dropwise thereto. The suspension is subsequently stirred overnight to complete the reaction and filtered. The filtrate is concentrated using a vacuum rotary evaporator. 110.5 g of a yellowish solution of 1,2-bis[4-(2-methoxy-3,3-dimethyl-oxiranyl)-phenyl]-ethane in 1,2-dichlorobenzene are obtained, which is used in the next reaction without being further purified.

4) Hydrolysis 60 ml of dioxane and 15 ml of water are added to 110.5 g (0.05 mol tq) of the 1,2-dichlorobenzene solution of 1,2-bis[4-(2-methoxy-3,3-dimethyl-oxiranyl)-phenyl]-ethane from the previous reaction and the resulting mixture is heated to 40° C. The solution is then adjusted to a pH of approximately 2 by the dropwise addition of approximately 1.3 g of 16% hydrochloric acid and subsequently stirred for three hours. The aqueous phase is separated off and the organic phase is washed twice with water. The organic phase is concentrated using a vacuum rotary evaporator and then dried under a high vacuum. The yellow oil obtained slowly crystallises out. The crystals are recrystallised twice from a small amount of ethyl acetate. 5.0 g of white crystals, which melt at 98.3-99.3° C., are obtained. In the $^1$H-NMR spectrum, the product 1,2-bis[4-(2-hydroxy-2-methyl-propionyl)-phenyl]-ethane is isomerically pure. A further 4.4 g of white crystals can be recovered from the mother liquors.

Elemental analysis: $C_{22}H_{26}O_4$

|  | % C |  | % H |
|---|---|---|---|
| calculated: | 74.55 | calculated: | 7.39 |
| found: | 74.38 | found: | 7.44 |

EXAMPLE 3

Preparation of 2-hydroxy-1-(4-{1-[4-(2-hydroxy-2-methyl-propionyl)-phenyl]-1-methyl-ethyl}-phenyl)-2-methyl-propan-1-one

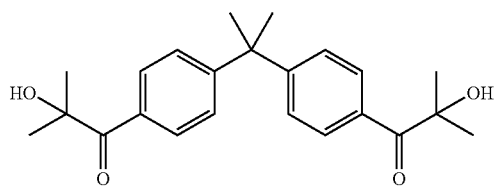

1) Friedel-Crafts Reaction 25.0 g (0.127 mol) of 2,2-diphenylpropane, 31.2 g (0.293 mol) of isobutyric acid chloride aund 150 ml of 1,2-dichlorobenzene are combined and cooled to from 5 to 0° C. using an ice-bath. 40.8 g (0.306 mol) of aluminium chloride are then added in small portions, in the course of approximately four hours, at an internal temperature of from 5 to 0° C. HCl gas is evolved. Stirring at an internal temperature of from 0 to 5° C. is then carried out for approximately 20 hours. At the end of that period all the aluminium chloride has dissolved. The dark-brown reaction mixture is subsequently poured into ice and water and extracted by stirring. The two phases are separated in a separating funnel. The organic phase is washed with water and then concentrated at approximately 60° C. and approximately 25 mbar using a vacuum rotary evaporator. 58.3 g of a dark-red oil are obtained. The product, an isomeric mixture in which the chief component is 2,2-bis[4-(2-methyl-propionyl)-phenyl]-propane, is used in the next reaction without being further purified. Found according to GC and $^1$H-NMR spectrum are 89% p,p isomer, 10% m,p isomer and 1% m,m isomer, without the solvent 1,2-dichlorobenzene.

2) Enol Bromination 54.9 g (0.12 mol tq) of the solution of 2,2-bis[4-(2-methyl-propionyl)-phenyl]-propane from the Friedel-Crafts reaction are diluted with 150 ml of chlorobenzene, and 0.1 g of chlorosulfonic acid is added. Subsequently, 38.4 g (0.12 mol) of bromine, diluted with 30 ml of chlorobenzene, are slowly added dropwise at room temperature. The solution is then stirred overnight and then concentrated at approximately 60° C. and approximately 25 mbar using a vacuum rotary evaporator. 87.5 g of a dark-red oil are obtained. The product, a solution of an isomeric mixture in 1,2-dichlorobenzene in which the chief component is 2,2-bis[4-(2-bromo-2-methyl-propionyl)-phenyl]-propane, is used in the next reaction without being further purified.

3) Hydrolysis 36. 8 g (0.276 mol) of 30% NaOH and 40 g of deionised water and 40 g of methanol are combined and then heated to 55° C. using an oil bath. While stirring well, 83.9 g (0.115 mol tq) of the crude product 2,2-bis[4-(2-bromo-2-methyl-propionyl)-phenyl]-propane from the bromination reaction, diluted with 60 g of toluene and with 20 g of methanol, are then added dropwise in the course of approximately one hour. The alkaline mixture (approximately pH 12) is then stirred for approximately one hour at 55-60° C. The conversion is checked using a $^1$H-NMR sample. The mixture is then cooled to 30° C. and adjusted to a pH of approximately 1-2 by the dropwise addition of approximately 13.3 g of 16% hydrochloric acid. The mixture is subsequently stirred for approximately 45 minutes. When the hydrolysis is complete, the reaction mixture is rendered neutral with a small amount of dilute sodium hydroxide solution. The two phases are separated in a separating funnel. The organic phase is extracted with 200 ml of water and then concentrated using a vacuum rotary evaporator. 55 g of a dark-colored oil are obtained. The oil is diluted with a small amount of ethyl acetate and purified by flash chromatography on Merck silica gel 60 (0.040-0.063 mm). A 1:4 mixture of ethyl acetate: hexane is used as eluant. 33.0 g of yellow crystals are isolated as the main fraction. The crystals are subjected to chromatography and then recrystallised from 32 g of toluene. 23.6 g of faintly yellowish crystals are obtained which melt at 95.9-97.3° C. In the $^1$H-NMR spectrum, the product 2,2-bis[4-(2-hydroxy-2-methyl-propionyl)-phenyl]-propane is isomerically pure.

EXAMPLE 4

Preparation of a mixture of 2-methoxy-1-(4-{1-[4-(2-methoxy-2-methyl-propionyl)-phenyl]-ethyl}-phenyl)-2-methyl-propan-1-one and 2-methoxy-1-{4-[4(2-methoxy-2-methyl-propionyl)-benzyl]-phenyl}-2-methyl-propan-1-one

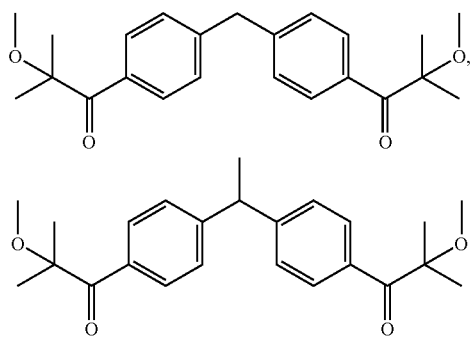

97.5 g (0.272 mol) of bis[4-(2-hydroxy-2-methyl-propionyl)-phenyl]-methane (isomeric mixture with water of crystallisation) are dissolved in 150 ml of dimethyl sulfoxide. 154.5 g (1.088 mol) of methyl iodide are added to that solution. The resulting solution is rapidly added dropwise to 850 ml of dimethyl sulfoxide. Simultaneously, 72.6 g (0.544 mol) of 30% NaOH are added dropwise. The temperature is maintained at 16-20° C. The solution turns blue and has a pH of 7-8. A further 72.6 g (0.544 mol) of 30% NaOH are added dropwise to that solution, at the end of which the pH is approximately 10. The resulting suspension is poured into ice and diethyl ether, diluted with 200 ml of toluene and stirred. The aqueous phase is separated off and extracted with 100 ml of toluene. The organic phase is washed with water and then concentrated using a vacuum rotary evaporator. 97.2 g of oil are obtained, which according to the $^1$H-NMR spectrum and TLC is a mixture. The mixture is purified on a silica gel column. A 1:4 mixture of ethyl acetate:hexane is used as eluant. The fractions obtained are checked by a $^1$H-NMR spectrum and TLC. The main fraction begins to crystallise. The crystals are recrystallised from hexane. 17.5 g of white crystals are obtained which melt at 56.2-58.4° C. In the $^1$H-NMR spectrum, the product is identified as 1,1-bis[4-(2-methoxy-2-methyl-propionyl)-phenyl]-ethane in isomerically pure form. The next fraction is a mixture and crystallises on seeding. The crystals are recrystallised from hexane. 9.9 g of white crystals are obtained which melt at 56.1-57.5° C. In the $^1$H-NMR spectrum, the product is again identified as 1,1-bis[4-(2-methoxy-2-methyl-propionyl)-phenyl]-ethane. The concentrated mother liquors, 13.7 g of a yellowish oil, prove according to TLC and the $^1$H-NMR spectrum to be in the form of a mixture of bis[4-(2-methoxy-2-methyl-propionyl)-phenyl]-methane and 1,1-bis[4-(2-methoxy-2-methyl-propionyl)-phenyl]-ethane in a ratio of approximately 60% to 40%.

Elemental analysis: $C_{24}H_{30}O_4$

|  | % C |  | % H |
|---|---|---|---|
| calculated: | 75.36 | calculated: | 7.91 |
| found: | 75.09 | found: | 7.98 |

EXAMPLE 5

Preparation of 2-methoxy-1-{4-[4-(2-methoxy-2-methyl-propionyl)-phenoxy]-phenyl}-2-methyl-propan-1-one

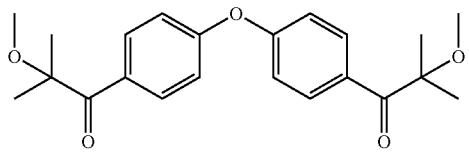

89.0 g (0.26 mol) of bis[4-(2-hydroxy-2-methyl-propionyl)-phenyl] ether are dissolved in 300 ml of dimethyl sulfoxide. 147.6 g (1.04 mol) of methyl iodide are added to that solution. The resulting solution is rapidly added dropwise to 750 ml of dimethyl sulfoxide. Simultaneously, 69.3 g (0.52 mol) of 30% NaOH are added dropwise. The temperature is maintained at 16-20° C. The solution turns yellow and has a pH of 7-8. A further 69.3 g (0.52 mol) of 30% NaOH are added dropwise to that solution, at the end of which the pH is approximately 11. The resulting suspension is poured into ice and diethyl ether, diluted with 200 ml of toluene and stirred. The aqueous phase is separated off and extracted with 100 ml of toluene. The organic phase is washed with water and then concentrated using a vacuum rotary evaporator. 96 g of an orange oil are obtained, which according to TLC is a mixture. The mixture is purified on a silica gel column. A 1:4 mixture of ethyl acetate:hexane is used as eluant. The fractions obtained are checked by a $^1$H-NMR spectrum and TLC. 61.3 g of yellowish oil are obtained as the main fraction. The oil slowly begins to crystallise when cold. The crystals are recrystallised twice from a small amount of hexane. 43.9 g of white crystals are obtained which melt at 54-56° C. In the $^1$H-NMR spectrum, the product is identified as bis[4-(2-methoxy-2-methyl-propionyl)-phenyl] ether.

Elemental analysis: $C_{22}H_{26}O_5$

|  | % C |  | % H |
|---|---|---|---|
| calculated: | 71.33 | calculated: | 7.07 |
| found: | 71.37 | found: | 7.13 |

EXAMPLE 6

Preparation of 2-methyl-1-{4-[4-(2-methyl-2-trimethylsilanyloxy-propionyl)-phenoxy]-phenyl}-2-trimethylsilanyloxy-propan-1-one

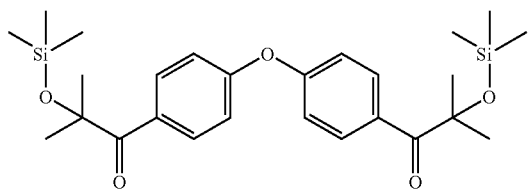

17.12 g (0.050 mol) of bis[4-(2-hydroxy-2-methyl-propionyl)-phenyl] ether are dissolved in 300 ml of methylene chloride. A spatula tip of 4-dimethylaminopyridine and 6.46 g (0.040 mol) of hexamethyldisilazane from Fluka are then added. 4.35 g (0.040 mol) of chlorotrimethylsilane from Fluka are then added dropwise at room temperature in the course of 15 minutes. The suspension is subsequently stirred for 2 hours and filtered. The filtrate is concentrated using a vacuum rotary evaporator. The oil is purified on a silica gel column by means of flash chromatography. A 1:9 mixture of ethyl acetate:hexane is used as eluant. 23.3 g of oil are obtained. In the $^1$H-NMR spectrum, the product is identified as bis[4-(2-trimethylsilanyloxy-2-methyl-propionyl)-phenyl] ether.

Elemental analysis: $C_{26}H_{38}O_5Si_2$

|  | % C |  | % H |
|---|---|---|---|
| calculated: | 64.16 | calculated: | 7.87 |
| found: | 64.27 | found: | 7.81 |

EXAMPLE 7

Preparation of 2-methyl-1-{4-[4-(2-methyl-2-trimethylsilanyloxy-propionyl)-benzyl]-phenyl}-2-trimethylsilanyloxy-propan-1-one

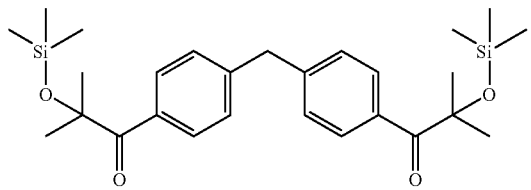

17.92 g (0.050 mol) of bis[4-(2-hydroxy-2-methyl-propionyl)-phenyl]-methane are dissolved in 300 ml of methylene chloride. A spatula tip of 4-dimethylaminopyridine and 12.92 g (0.080 mol) of hexamethyldisilazane from Fluka are then added. 8.70 g (0.080 mol) of chlorotrimethylsilane from Fluka are then added dropwise at room temperature in the course of 15 minutes. The suspension is subsequently stirred for 2 hours and filtered. The filtrate is concentrated using a vacuum rotary evaporator. 25.4 g of oil remain. The oil is purified on a silica gel column by means of flash chromatography. A 1:9 mixture of ethyl acetate:hexane is used as eluant. 18.0 g of white crystals are obtained which melt at 52-54° C. In the $^1$H-NMR spectrum, the product is identified as bis[4-(2-trimethylsilanyloxy-2-methyl-propionyl)-phenyl]-methane.

Elemental analysis: $C_{27}H_{40}O_4Si_2$

| | % C | | % H |
|---|---|---|---|
| calculated: | 66.90 | calculated: | 8.32 |
| found: | 66.93 | found: | 8.49 |

Application Examples

EXAMPLE A1

Overprint Coating Formulation with Aminoacrylate

| Component | % by wt. |
|---|---|
| Ebecryl 605 (bisphenol A epoxyacrylate, diluted with 25% TPGDA (UCB)) | 30.0 |
| Ebecryl 7100 (aminoacrylate (UCB)) | 10.0 |
| Ebecryl 40 (pentaerythritol ethoxylate tetraacrylate (UCB)) | 5.0 |
| OTA 480 (glycerol propoxylate triacrylate (UCB)) | 30.0 |
| TPGDA (tripropylene glycol diacrylate) | 24.0 |
| Ebecryl 1360 (silicone acrylate) | 0.5 |
| Dow Corning 57 (silicone additive, flow improver) | 0.5 |
| Σ | 100.0 |

In each case a weight of 0.6 g of photoinitiator per 10 g of formulation is used.

UV Exposure Apparatus (IST):
2 medium-pressure mercury lamps, each 120 W/cm and each having a metal oxide vaporized mirror.
Variable-speed conveyor belt.
Curing Rate:
Determination of the resistance to wiping of the cured clearcoats, data in m/min conveyor belt speed of the UV exposure apparatus;
layer thickness 6 μm (Erichson doctor knife apparatus) applied to cardboard.
Gloss:
Measurement of gloss 2 hours after curing at a conveyor belt speed of the UV exposure apparatus of 10 m/min;
layer thickness 100 μm (hand-held doctor knife) applied to white-coated chipboard panels.
The measuring angle in the gloss measurement is 20°.
Odour Evaluation:
Curing of the clearcoats at a predetermined curing rate at a belt speed of 30 m/min.
Layer thickness: 6 μm applied to aluminium foil.
Evaluation: 0=odourless, 1=very faint, 2=faint, 3=distinct, 4=strong, 5=very strong.
Inherent odour of the substrate: 1.

Evaluation of the Resistance to Solvent:
Layer thickness: 6 μm applied to cardboard.
Curing at a conveyor belt speed of the UV exposure apparatus of 30 m/min.
The samples are rubbed with a small piece of acetone-impregnated felt (50 "double rubs").
Evaluation: 0=no damage, 1=very slight, 2=slight, 3=clear, 4=significant, 5=very significant.

TABLE 1

Overprint coating formulation with aminoacrylate.

| Photoinitiator Example | Curing rate [m/min] | Gloss [%] | Odour evaluation | Evaluation of resistance to solvent |
|---|---|---|---|---|
| Example 1 | 140 | 87 | 3 | 0-1 |
| Example 2 | 120 | 85 | 2 | 1 |
| Example 3 | 90 | 87 | 2 | 1 |
| Example 4 | 100 | 86 | 2 | 0-1 |
| Example 5 | 120 | 87 | 2 | 1 |
| Darocur 1173 | 70 | 85 | 3 | 1-2 |
| Irgacure 184 | 50 | 86 | 3 | 2 |

Table 1 shows the good curing rate of the photoinitiators according to the invention.

Darocur 1173: 2-hydroxy-2-methyl-1-phenylpropan-1-one (Ciba)

Irgacure 184: (1-hydroxy-cyclohexyl)-phenyl-ketone (Ciba)

EXAMPLE A2

Overprint Coating Formulation Without Aminoacrylate

| Component | % by wt. |
|---|---|
| Ebecryl 605 | 35.0 |
| Ebecryl 40 | 10.0 |
| OTA 480 | 30.0 |
| TPGDA | 24.0 |
| Ebecryl 1360 | 0.5 |
| Dow Corning 57 | 0.5 |
| Σ | 100.0 |

TABLE 2

| Photoinitiator Example | Curing rate [m/min] | Gloss [%] | Odour evaluation | Evaluation of resistance to solvent |
|---|---|---|---|---|
| Example 1 | 70 | 87 | 3 | 0-1 |
| Example 2 | 60 | 85 | 2 | 0-1 |
| Example 3 | 40 | 87 | 3 | 0-1 |
| Example 4 | 60 | 86 | 2 | 0-1 |
| Example 5 | 60 | 87 | 2 | 0 |
| Darocur 1173 | 30 | 85 | 3 | 1-2 |
| Irgacure 184 | 20 | 86 | 3 | 2 |

EXAMPLE A3

Blue Flexographic Printing Ink Formulation

| Component | % by wt. |
|---|---|
| IRR 440 (oligomeric acrylate as base resin for flexographic printing ink (UCB)) | 26.9 |
| OTA 480 (a glycerol propoxylate triacrylate (UCB)) | 19.0 |
| Ebecryl 645 (modified bisphenol A epoxyacrylate, diluted with 25% TPGDA (UCB)) | 18.0 |
| 1,6-hexanediol diacrylate | 13.0 |
| Ebecryl 220 (hexafunctional aromatic urethane acrylate (UCB)) | 10.0 |
| Ebecryl 168 (acidic methacrylate, adhesive agent) | 1.3 |
| Dow Corning 57 (silicone additive, flow agent) | 0.7 |
| Irgalite Blue GLO (copper phthalocyanine (β)(Ciba)) | 11.1 |
| Σ | 100.0 |

UV Exposure Apparatus (IST):
1 medium-pressure mercury lamp, 120 W/cm, variable-speed conveyor belt
  Substrate: white PE film (75 μm)
  Application: test structure, 1.38 g/m$^2$, corresponds to an optical density of 1.45
  Properties Tested:
throughcure (TC), surface cure (SF), nail test (Nail), adhesion (tape test (AD)), solubility (SO).

TABLE 3

| | | ...m/min Hg 1 × 120 W/cm (IST) | | | | | |
|---|---|---|---|---|---|---|---|
| Photoinitator | Conc. % | TC | Nail | AD | SF | SO | Comments |
| Irgacure 369 | 5.0 | 40 | +/− | + | 80 | + | |
| | 7.0 | 140 | +/− | + | 200 | + | |
| Irgacure 907 + Speedcure ITX | 5.0 0.5 | 50 | +/− | + | 70 | + | |
| Irgacure 907 + Speedcure ITX | 7.0 0.5 | 100 | +/− | + | 140 | + | |
| Irgacure 1300 | 5.0 | 20− | − | + | 20− | + | |
| | 7.0 | 50 | − | + | 70 | + | |
| Example 1 | 5.0 | 100 | +/− | + | 100 | + | |
| | 7.0 | 190 | +/− | + | 180 | + | |
| Example 5 | 5.0 | 40 | +/− | + | 60 | + | |
| | 7.0 | 120 | +/− | + | 130 | + | |
| Example 2 | 5.0 | 80 | +/− | + | 100 | + | |
| | 7.0 | 110 | +/− | + | 100 | +/− | + at 45°/− at 25° C. |
| Example 4 | 5.0 | 80 | +/− | + | 90 | + | |
| | 7.0 | 110 | +/− | + | 110 | + | |

Irgacure 369: 2-benzyl-2-dimethylamino-1-(4-morpholinophenyl)-butanone-1 (Ciba)
Irgacure 907: 2-methyl-[4-(methylthio)phenyl]-2-morpholinopropan-1-one (Ciba)
Irgacure 1300: 30% Irgacure 369 + 70% 2,2-dimethoxy-1,2-diphenylethan-1-one (IRGACURE 651)
Speedcure ITX: isopropyl thioxanthone (QUANTACURE ITX, Great Lakes Fine Chemicals LTD., Cheshire, England)

EXAMPLE A4

Powder Coating Formulation

| Component | % by wt. |
|---|---|
| Uracross P3125 (unsaturated polyester resin from DSM) | 76.5 |
| Uracross P3307 (vinyl ether polyurethane resin from DSM) | 20 |
| Worlee add 902 (flow agent from Worlée Chemie) | 0.5 |
| Resiflow PV5 (flow agent from Worlée Chemie) | 1.0 |
| Photoinitiator | 2.0 |
| Σ | 100.0 |

Extruded at 70° C. (twin-screw extruder prism TS 16)

The clear powder coating is applied to white-coated chipboard panels and to glass. (Wagner turbo gun); Layer thickness: 75±5 μm The coated samples are fused under an IR lamp (2 min., 140° C) and cured.

UV exposure apparatus (IST):

Hg— and Fe-doped lamps, each 240 W/cm,

Variable-speed conveyor belt (curing rate: 10, 20 or 40 m/min)

Test Procedure:

König pendulum hardness according to DIN 53157.

The measurement is carried out immediately after curing (0 h) and after 24 h.

Methyl ethyl ketone Blister Test.

The time taken for the coating to begin to lift is measured.

Methyl ethyl ketone Soak Test: the percentage weight loss is measured.

Yellowing: The b* value is determined immediately after curing

TABLE 4

| Photoinitiator | Curing rate m/min | Pendulum hardness (sec) 0 h | Pendulum hardness (sec) 24 h | MEK blister test (min) 0 h | MEK blister test (min) 24 h | MEK soak test % 0 h | b* value 0 h |
|---|---|---|---|---|---|---|---|
| Irgacure 184 | 10 | 132 | 146 | 33 | 35 | 1.4 | 1.1 |
| | 20 | 125 | 137 | 28 | 28 | 0.2 | |
| | 40 | 115 | 126 | 15 | 14 | −0.7 | |
| Example 1 | 10 | 90 | 120 | 20 | 29 | 0.9 | 2.2 |
| | 20 | 88 | 113 | 16 | 17 | 1 | 1.8 |
| | 40 | 78 | 106 | 08 | 10 | −1.2 | 0.8 |

EXAMPLE A5

UV Inkjet Test Formulation

A pigment concentrate is prepared in a bead mill using the raw materials shown in Table 5. 15 parts of the pigment concentrate are mixed with 79.50 parts of the reactive diluent (Viajet 400, UCB), 3.40 parts levelling agent (DOW Corning 57, DOW Corning), and 6 or 8 parts of the photoiniator, to give the final ink.

TABLE 5

Composition of the pigment concentrate.

| Raw Material | Parts |
|---|---|
| Viajet 100 (UCB) | 78.45 |
| Irgalite Blue GLO (Ciba) | 20.00 |
| Florstab UV1 (Kromachem) | 1.00 |
| Solsperse 5000 (Avecia) | 0.55 |

Viajet 100 is a unique, 100% solids pigment grinding vehicle for use in producing pigment concentrates for UV inkjet inks.

Florstab is an in-can stabilizer for UV-curing systems

Curing Performance of the UV Inkjet Test Formulations

The inks are applied to metallized paper using a 12 μm K-bar. Upon exposure to the UV light of 2 medium pressure mercury lamps (120 W/cm each), the surface cure of the inks is tested (dry rub test with paper tissue). The cure speed corresponds to the maximum speed of the conveyor belt of the UV curing unit, at which the ink is completely cured and tack free. The observed data are shown in Table 6.

TABLE 6

Cure speed of the UV Inkjet test formulations.

| Photoinitiator | Cure Speed [m/min] | |
|---|---|---|
| | 6% | 8% |
| Irgacure 369 | 20 | 30 |
| Irgacure 907/ITX (4:1) | 20 | 30 |
| Example 1 | 30 | 50 |

What is claimed is:

1. A process for the production of a scratch-resistant durable surface, wherein a composition comprising
   (A) an ethylenically unsaturated compound that contains at least one aminoacrylate,
   (B) 0.5 to 10% by weight photoinitiator of formula V

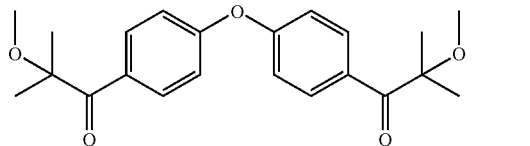

(C) optionally further binders or additives,
   (D) optionally further photoinitiators or co-initiators is applied to a support, and curing of the composition is carried out either solely by irradiation with electromagnetic radiation of a wavelength ranging from 200 nm into the NIR or IR region, or by irradiation with electromagnetic radiation and prior, simultaneous and/or subsequent action of heat wherein the curing step occurs at a cure rate of at least 100 meters/minute and the cure rate is effected at a lamp out put of at least 120 W/cm.

2. A composition comprising
   (A) an ethylenically unsaturated compound that contains at least one aminoacrylate,
   (B) 0.5 to 10% by weight photoinitiator of formula V

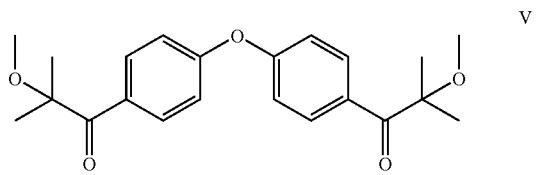

(C) optionally further binders or additives,
   (D) optionally further photoinitiators or co-initiators.

3. The composition according to claim 2, wherein the aminoacrylate is at least 10% by weight.

4. The composition according to claim 2 which is selected from the group consisting of pigmented or unpigmented surface coatings, overprint coatings, formulations for printing inks, powder coatings, inkjet inks, fine layers (gel coats), composite materials and glass fibre cable coatings.

5. A process for the production of a scratch-resistant durable surface, wherein a composition according to claim 2 is applied to a support, and curing of the formulation is carried out either solely by irradiation with electromagnetic radiation of a wavelength ranging from 200 nm into the NIR or IR region, or by irradiation with electromagnetic radiation and prior, simultaneous and/or subsequent action of heat wherein the curing step occurs at a cure rate of at least 100 meters/minute.

6. The process according to claim 1 wherein a composition is applied to a support as an overprint coating.

* * * * *